United States Patent [19]

Urquhart et al.

[11] Patent Number: 4,969,872
[45] Date of Patent: Nov. 13, 1990

[54] INTRAVENOUS SYSTEM FOR DELIVERING A BENEFICIAL AGENT WITH DELIVERY RATE CONTROL VIA PERMEABLE SURFACE AREA VARIANCE

[75] Inventors: John Urquhart, Palo Alto; Felix Theeuwes, Los Altos, both of Calif.

[73] Assignee: ALZA Corporation, Palo Alto, Calif.

[21] Appl. No.: 320,732

[22] Filed: Mar. 8, 1989

[51] Int. Cl.⁵ .............................................. A61M 37/00
[52] U.S. Cl. ...................................... 604/85; 604/251; 604/892.1
[58] Field of Search ...................................... 604/82–85, 604/131, 140, 141, 246, 251, 255, 892.1, 890.1

[56] References Cited

U.S. PATENT DOCUMENTS

| | | | |
|---|---|---|---|
| 3,760,984 | 9/1973 | Theeuwes | 222/95 |
| 3,845,770 | 11/1974 | Theeuwes et al. | 128/260 |
| 3,921,636 | 11/1975 | Zaffaroni | 128/260 |
| 3,987,790 | 10/1976 | Eckenhoff et al. | 128/260 |
| 3,995,631 | 12/1976 | Higuchi et al. | 128/260 |
| 4,066,747 | 1/1978 | Capozza | 424/78 |
| 4,070,347 | 1/1978 | Schmitt | 260/77.5 D |
| 4,093,708 | 6/1978 | Zaffaroni et al. | 424/15 |
| 4,111,202 | 9/1978 | Theeuwes | 128/260 |
| 4,136,692 | 1/1979 | Goldowsky | 604/251 |
| 4,190,642 | 2/1980 | Gale et al. | 424/19 |
| 4,246,397 | 1/1981 | Choi | 528/380 |
| 4,281,654 | 8/1981 | Shell et al. | 128/260 |
| 4,303,637 | 12/1981 | Shell et al. | 424/14 |
| 4,304,765 | 12/1981 | Shell et al. | 424/14 |
| 4,317,473 | 3/1982 | Gaydos | 604/251 X |
| 4,432,964 | 2/1984 | Shell et al. | 424/14 |
| 4,474,575 | 10/1984 | Eckenhoff et al. | 604/131 |
| 4,478,818 | 10/1984 | Shell et al. | 424/14 |
| 4,505,703 | 3/1985 | Gale et al. | 604/317 |
| 4,511,353 | 4/1985 | Theeuwes | 604/85 |
| 4,539,004 | 9/1985 | Eckenhoff et al. | 604/131 |
| 4,552,555 | 10/1985 | Theeuwes | 604/56 |
| 4,715,850 | 12/1987 | Tran | 604/82 |
| 4,740,103 | 4/1988 | Theeuwes | 604/83 |
| 4,740,200 | 4/1988 | Theeuwes | 604/85 |
| 4,740,201 | 4/1988 | Theeuwes | 604/85 |
| 4,865,845 | 9/1989 | Eckenhoff et al. | 424/424 |

Primary Examiner—John D. Yasko
Assistant Examiner—Adam J. Cermak
Attorney, Agent, or Firm—D. Byron Miller; Edward L. Mandell; Steven F. Stone

[57] ABSTRACT

A drug formulation chamber for an intravenous administration set is provided. The intravenous administration set includes a container of an IV fluid, a drip chamber, a drug formulation chamber, and an adapter-needle assembly. The drug formulation chamber houses a diffusional or an osmotically driven drug delivery device. The osmotically driven delivery device has a semipermeable, microporous or diffusional wall which surrounds a compartment containing the drug. Drug is delivered through an orifice in the semipermeable/microporous wall or through the diffusional wall itself, into the IV fluid. The device delivers drug into the IV fluid at a rate that is independent of the flow rate of IV fluid through the formulation chamber. The rate of drug delivery is controlled by variably adjusting the surface area of the semipermeable/microporous/diffusional wall that is exposed to the IV fluid flowing through the drug formulation chamber.

54 Claims, 2 Drawing Sheets

U.S. Patent  Nov. 13, 1990  Sheet 1 of 2  4,969,872
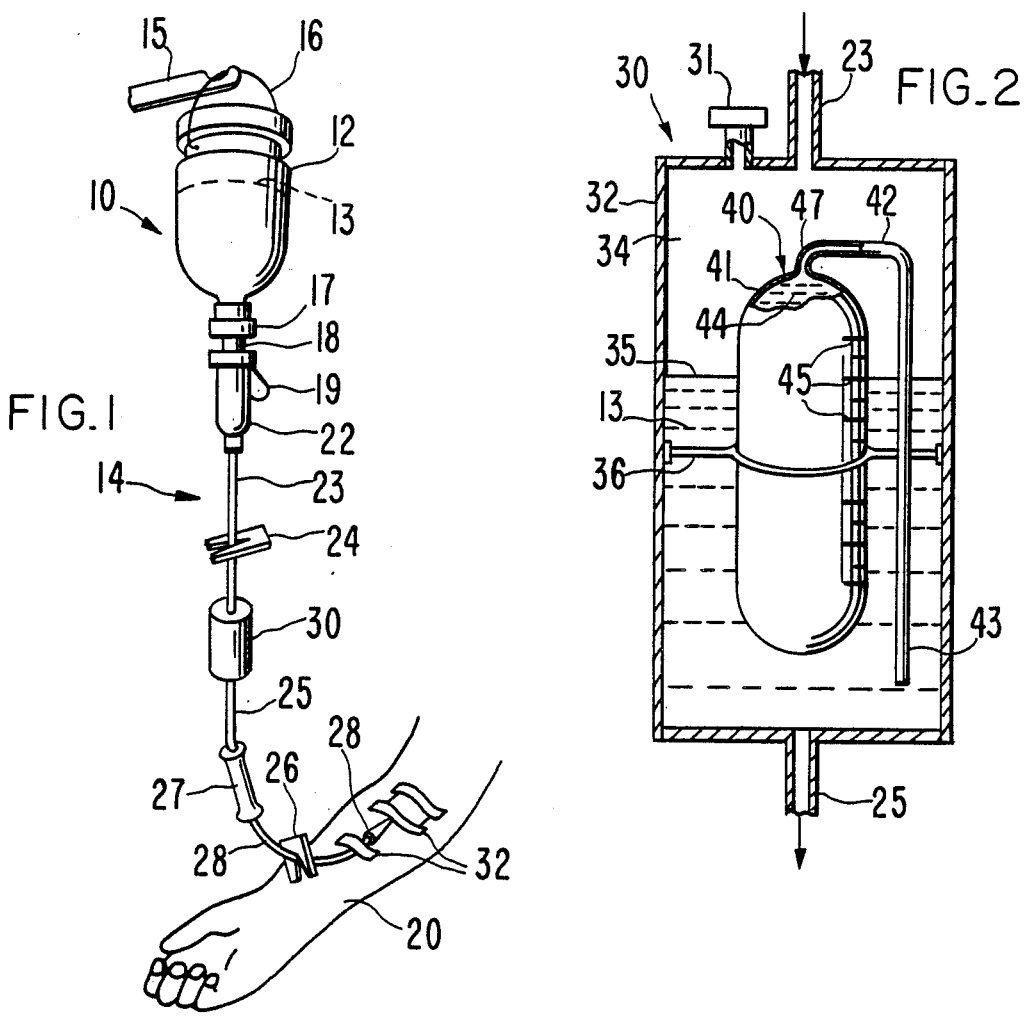
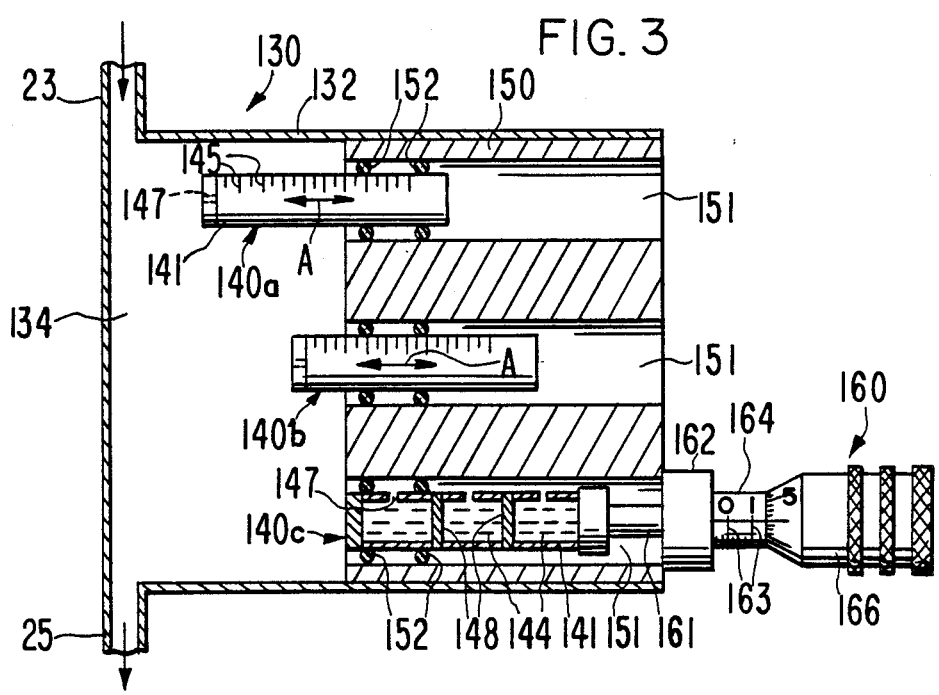

INTRAVENOUS SYSTEM FOR DELIVERING A BENEFICIAL AGENT WITH DELIVERY RATE CONTROL VIA PERMEABLE SURFACE AREA VARIANCE

BACKGROUND OF THE INVENTION

1. Field of the Invention

This invention pertains to an intravenous delivery system, and to a formulation chamber containing a drug delivery device. The invention relates also to a method of parenterally (e.g., intravenously) administering a drug, and to a method of forming the drug during parenteral administration.

2. Description of the Prior Art

The parenteral administration of medical liquids is an established clinical practice. The liquids are administered particularly intravenously, and the practice is used extensively as an integral part of the daily treatment of medical and surgical patients. The liquids commonly administered include blood and blood substitutes, dextrose solutions, electrolyte solutions and saline. Generally the liquids are administered from an intravenous (IV) delivery system having a container suspended above the patient, with the liquid flowing through a catheter hypodermic needle set to the patient.

The administration of liquids intravenously is a valuable and important component that contributes to the optimal care of the patient. However, it does not easily provide a satisfactory means and method for administering concomitantly therewith a beneficial agent, such as a drug. Beneficial agents have been administered intravenously by one of the following methods: (1) temporarily removing or disconnecting the IV system administering the agent to the patient, then administering the drug by hypodermic injection (either into the disconnected IV line or directly into the vein of the patient), followed by reinserting the IV system into the patient; (2) adding the agent to the IV liquid in the container which is then carried by the flow of the liquid to the patient; (3) adding the agent to an IV liquid in a secondary container (called a partial fill) that is then connected to the primary IV line; (4) adding the agent to an IV liquid contained in a piggyback vial which is subsequently connected to the primary IV line; or (5) administering intravenously an IV liquid containing a beneficial agent using a pump. While these techniques are used, they have major disadvantages. For example, they often require preformulation of the agent medication by the hospital pharmacist or nurse. They often require separate connections for joining the drug flow line to the primary intravenous line which further complicates intravenous administration. The use of pumps can produce pressures that can vary at the delivery site and the pressure can give rise to thrombosis. Finally, the rate of agent delivery to the patient often is unknown as it is not rate-controlled agent delivery but rather is dependent on the rate of IV fluid flow.

Eckenhoff et al in U.S. Pat. No. 4,474,575 discloses an IV administration set (FIG. 6) providing excellent control over the rate at which beneficial agent is administered to a patient. Unfortunately, the device disclosed by Eckenhoff et al is not easily adapted to a conventional IV administration set which typically includes an IV fluid container, a drip chamber for visually determining the rate of IV fluid flow from the container, a bacterial filter, and terminating in an adaptor-needle assembly that is inserted into the vein of a warm-blooded animal (e.g., a human patient). In order to adapt the Eckenhoff device to a conventional IV administration set, a secondary IV fluid line must be connected into the primary IV line which complicates the intravenous administration.

In response to these difficulties, Theeuwes in U.S. Pat. No. 4,511,353 (and in related U.S. Pat. Nos. 4,740,103; 4,740,200 and 4,740,201) developed a formulation chamber adapted to easily fit into a conventional IV administration set. The formulation chamber is adapted to contain a drug delivery device for delivering a drug or other beneficial agent into the IV fluid flowing through the formulation chamber. The drug delivery device within the formulation chamber is selected from elementary osmotic pumps (FIGS. 2a, 2b, 9, 10, and 11) release rate controlling membranes surrounding a drug reservoir (FIGS. 3–5, 12 and 13) and a polymer matrix containing the drug, the drug being able to diffuse through the matrix into the flowing IV fluid (FIGS. 6–8). All of these devices provide the advantage of controlling the rate at which the drug or other beneficial agent is released into the IV fluid, independently of the rate at which the IV fluid flows through the formulation chamber.

While these devices represent a significant advance in the art, there remains a need for a drug formulation chamber which can provide an even higher degree of control over the rate at which a beneficial agent, such as a drug, is introduced into an IV fluid flowing in a standard IV administration set.

Accordingly, it is an object of this invention to provide a parenteral (e.g., intravenous) delivery system which delivers an agent at a controlled rate into a flowing parenteral fluid for optimizing the care of an animal (e.g., a human) whose prognosis benefits from parenteral delivery.

It is another object of the invention to provide an intravenous delivery system having an agent formulation chamber which contains an agent delivery device for admitting agent at a rate controlled by the delivery device, instead of the flow rate of intravenous fluid through the system, for optimizing the care of a patient on intravenous delivery.

Another object of the invention is to provide an intravenous therapeutic system including a container of an intravenous medical fluid and a drug formulation chamber which contains an agent delivery device which can deliver drug, to a flowing IV fluid, at a rate which is variable and which is accurately controlled by the device.

SUMMARY OF THE INVENTION

These and other objects are met by an agent formulator, a parenteral administration system and a method for the controlled parenteral administration of a beneficial agent to an animal. The agent formulator comprises a chamber having fluid inlet and fluid outlet means to maintain a continuous flow of a parenterally acceptable fluid therethrough. An agent delivery device is positioned in the chamber. The delivery device contains a beneficial agent to be delivered into the parenteral fluid.

In one embodiment, the delivery device has a semipermeable or microporous wall portion that is permeable to the parenteral fluid and substantially impermeable to the agent. The delivery device of the first embodiment also has a passageway through which the agent is delivered into the fluid at a controlled rate. In a second embodiment, the delivery device has a diffusional wall portion which is hydrated by the parenteral fluid and permits the beneficial agent, which is soluble in the parenteral fluid, to diffuse through the wall portion at a controlled rate for delivery into the fluid. In a third embodiment, the delivery device comprises a polymer matrix containing a beneficial agent. The polymer matrix has the property of releasing the beneficial agent at a controlled rate over a period of time when exposed to the parenteral fluid.

The agent formulator also includes means for adjustably varying the surface area of the wall portion or matrix which is exposed to the fluid flowing through the chamber.

In operation of the first embodiment, the parenteral fluid flowing through the chamber contacts a predetermined area of the semipermeable or microporous wall portion and is imbibed therethrough. The imbibed fluid causes the agent to be delivered from the device through the passageway and into the flowing fluid. In the second embodiment, the parenteral fluid flowing through the chamber contacts a predetermined area of the diffusional wall portion causing the beneficial agent to diffuse therethrough. In the third embodiment, the parenteral fluid flowing through the chamber contacts a predetermined area of the polymer matrix causing the beneficial agent to be released into the fluid. In all embodiments, the beneficial agent is released by the delivery device at a rate which is variable, which is controlled substantially by the area of the wall portion exposed to the fluid or by the area of the matrix exposed to the fluid and which is substantially independent of the volumetric flow rate of the fluid flowing through the chamber.

Preferably, the beneficial agent comprises a drug and the agent formulator is positioned within an intravenous administration system including a container of a pharmaceutically acceptable intravenous fluid and an intravenous administration set used to deliver an intravenously acceptable fluid to a human patient.

The present invention also provides a method for the controlled parenteral administration of a beneficial agent to an animal. The method comprises the steps of:

(a) placing an agent delivery device in an agent formulation chamber having an inlet communicating with a container of a pharmaceutically acceptable parenteral fluid and an outlet communicating with the animal;

(b) allowing the parenteral fluid, which is a carrier for the agent, to flow from the container, through the chamber and into the animal.

In one embodiment, the delivery device has a semipermeable or microporous wall portion that is permeable to the parenteral fluid and substantially impermeable to the agent. The delivery device of the first embodiment also includes a passageway through which the agent is delivered into the fluid. In a second embodiment, the delivery device has a diffusional wall portion which is hydrated by the parenteral fluid and permits the agent to diffuse through the wall portion at a controlled rate for delivery into the fluid. In a third embodiment, the delivery device comprises a polymer matrix containing the beneficial agent. The polymer matrix has the property of releasing the agent at a controlled rate over a period of time when exposed to the parenteral fluid.

The method also includes the step of adjustably varying the surface area of the wall portion or matrix which is exposed to the fluid flowing through the chamber.

In operation of the first embodiment, the fluid flowing through the chamber contacts a predetermined area of the semipermeable or microporous wall portion and is imbibed therethrough. This causes the beneficial agent to be delivered from the device through the passageway into the flowing fluid. In the second embodiment, the parenteral fluid flowing through the chamber contacts a predetermined area of the diffusional wall portion causing the beneficial agent to diffuse therethrough. In the third embodiment, the parenteral fluid flowing through the chamber contacts a predetermined area of the polymer matrix causing the beneficial agent to be released into the fluid. In all three embodiments, the agent is released at a rate which is variable, which is controlled substantially by the area of the wall portion or by the area of the matrix exposed to the fluid and which is substantially independent of the volumetric flow rate of the fluid flowing through the chamber. The method is effective to administer the beneficial agent to the animal in a beneficially effective amount over a prolonged period of time. Preferably, the method is used to deliver a drug intravenously to a human patient.

BRIEF DESCRIPTION OF THE DRAWINGS

FIG. 1 is a perspective view showing an agent formulator 30 and its use within an intravenous delivery system 10;

FIG. 2 is a sectional view of one embodiment of an agent formulator according to the present invention;

FIG. 3 is a sectional view of another embodiment of an agent formulator according to the present invention.

In the specification and the drawings, like parts in related Figures are identified by like numbers.

DETAILED DESCRIPTION OF THE INVENTION

Figure 4:
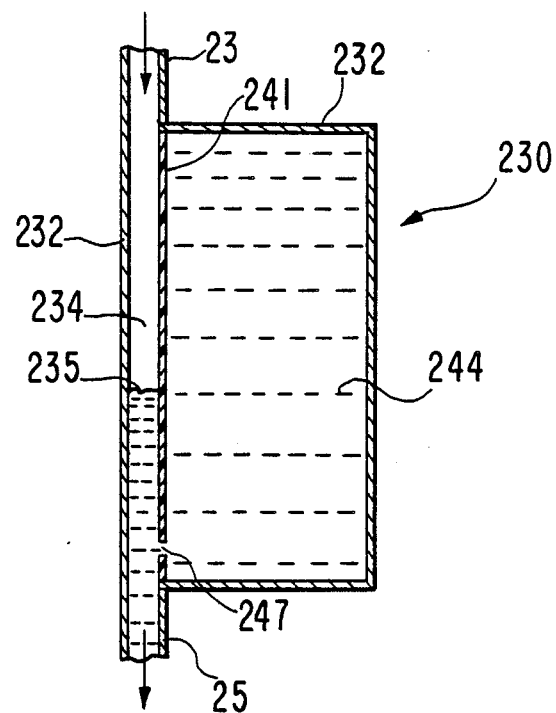
FIG. 4 is a sectional view of another embodiment of an agent formulator according to the present invention.

FIG. 1 illustrates an operative intravenous delivery system, generally designated by the numeral 10, showing the positioning of an agent formulator 30 therein. System 10 comprises a container 12 that contains a fluid 13 suitable for intravenous administration, and an administration set, generally designated 14. The fluid 13 in container 12 will typically be a medical fluid, i.e., a sterile solution such as an aqueous solution of dextrose, saline, and/or electrolytes. Fluid 13 is a vehicle for intravenous administration of a pharmaceutical agent to a recipient. Container 12 is manufactured from glass or plastic, and is preferably of the no air-tube vacuum type and thus it is used with an administration set that has an air inlet filter. Other types of containers such as the air-tube vacuum type, or the non-vented type, can be used for the intended purpose. These alternative containers do not require an air filter in the administration set 14. Container 12 can be rigid, semi-rigid or flexible in structure, and it is usually adapted to be hung neck-down from a hanger 15 by a handle 16 that connects or surrounds container 12. The neck of container 12 is covered by a closure 17, generally made of rubber and air-tight.

Administration set 14 and container 12 are interconnected by piercing closure 17 with one end of a hollow spike 18 attached to or formed as a part of administration set 14. Spike 18 is equipped with a side air vent 19. The other end of spike 18 is enlarged and fits snugly into a drip chamber 22. Drip chamber 22 traps air contained in the set 14 and facilitates adjusting the flow rate of intravenous fluid 13 from container 12 as the flow proceeds drop wise. The outlet at the bottom of drip chamber 22 is connected to a first segment of tubing 23 which fits into agent formulator 30, the details of which are presented in FIG. 2. A second segment of tubing 25 leads from agent formulator 30 to bacterial filter 27. A third segment of tubing 29 extends from filter 27 to an infusion agent receptor site, terminating in an adapter-needle assembly 28 that is inserted into a vein of a warm-blooded animal 20, shown as a human arm. Tape 32 holds adapter-needle assembly 28 firmly in place on the recipient's arm. The administration set can also include a pair of tubing clamps 24 and 26 located on either side of formulator 30 that may be used to govern or stop the flow of intravenous fluid through the intravenous delivery system 10.

Agent formulator 30, as seen in FIG. 2, is the unique component of the intravenous delivery system 10. Agent formulator 30 comprises a wall 32 forming a chamber 34. An air release valve 31 of a conventional design may optionally be provided in wall 32 for admitting or releasing air from chamber 34 in order to adjust the fluid level 35. An agent delivery device 40 is housed within the chamber 34. Device 40 contains a beneficial agent 44 to be delivered into the IV fluid 13. The beneficial agent 44 exhibits an osmotic pressure gradient across wall 41 of device 40 against the IV fluid 13 in chamber 34. The beneficial agent 44 can comprise an agent that exhibits an osmotic pressure gradient, or the agent 44 can comprise a drug mixed with an osmotically effective solute, such as sodium chloride, potassium chloride and the like, that exhibits an osmotic pressure substantially greater than the fluid in the formulator 30. A retaining means 36 keeps device 40 fixedly positioned within formulator 30, permitting the free passage of IV fluid through formulator 30. Wall 32 may be comprised of glass, plastic or the like, and is preferably a transparent material thereby enabling a nurse or other medical technician to see the level 35 of IV fluid 13 contained in formulator 30. Formulator 30 can also be manufactured as a two-piece unit with the delivery device 40 therein, or formulator 30 can be manufactured with a closable lid for admitting the delivery device 40.

As shown in FIG. 2, the exterior surface of wall 41 is provided with a plurality of marking lines 45 along its length. Because the wall 32 of formulator 30 is made of a transparent material, a medical technician can easily determine the air/liquid interface level 35 in relation to the markings 45 on delivery device 40. The interface level 35 may be adjusted in a number of different ways. For example, the wall 32 of formulator 30 may be comprised of a flexible and transparent material such as polyethylene or plasticized polyvinyl chloride. The tube 25 is first clamped closed and the formulator 30 is simply squeezed by the technician, thereby causing air within chamber 34 to be vented either into the fluid container 12 or through the air release valve 31. Alternatively, a squeeze bulb and catheter (not shown in the Figures) can be connected to valve 31. After allowing the chamber 34 to become completely filled with fluid 13, air can be forced into chamber 34 by pumping the squeeze bulb of the bulb/catheter set in order to lower the level 35 to the desired point. A check valve may also be provided in the balloon/catheter set which may be opened to release air from the chamber 34 in order to raise the level 35. Other known methods for adjusting the air/liquid interface level 35 within chamber 34 may also be utilized.

Agent delivery device 40, in the illustrated embodiment, may be an osmotic rate-controlled pump of the type described by Eckenhoff et al in U.S. Pat. No. 3,987,790. Device 40 has a semipermeable or microporous outer wall 41 which is permeable to fluid 13 and has a sufficent degree of impermeability to solute 44 to generate an osmotic pressure differential across wall 41. Wall 41 may be comprised of a material such as cellulose acylate, cellulose diacylate, cellulose triacylate, cellulose acetate, cellulose diacetate or cellulose triacetate. The outer wall 41 surrounds and forms an inner compartment containing the beneficial agent 44. Generally, when the outer wall 41 is comprised of a semipermeable or microporous membrane, the device 40 will have a passageway 47 extending through the outer wall 41 so that a solution of the drug or other beneficial agent can be pumped into chamber 34. In the illustrated embodiment, a hollow open-ended catheter 42 is connected with the passageway 47 through the semipermeable/microporous wall 41. The free end 43 of catheter 42 is positioned beneath device 40. In this way, beneficial agent 44 is delivered from device 40 through the hollow catheter 42 directly into the IV fluid 13.

When wall 41 is made of a semipermeable or microporous material that is permeable to the IV fluid 13, IV fluid enters chamber 34 and is imbibed through the portion of semipermeable/microporous wall 41 which is submerged in the IV fluid 13. The IV fluid is imbibed through wall 41 into device 40 which contains the beneficial agent 44 in a tendency toward osmotic equilibrium. The rate at which IV fluid enters device 40 is determined by the surface area of semipermeable/microporous wall 41 which is submerged in the IV fluid 13, as well as by the permeability of the wall 41 and the osmotic gradient across the wall 41. The IV fluid entering device 40 forms a suspension or a solution of agent 44 that is dispensed through the catheter 42 over a prolonged period of time. The delivery rate of agent 44 into the IV fluid is controlled by device 40 and is independent of the rate of IV fluid flow and the pH of the IV fluid in the chamber 34. In the embodiment illustrated in FIG. 2 which utilizes a semipermeable wall 12, beneficial agent 44 is delivered through catheter 42 into the liquid 13. However, it is also within the scope of the present invention to utilize a delivery device 40 having a passageway 47 at its bottom end, in which case no catheter 42 is required.

Other known osmotically powered agent dispensing devices may also be substituted for the illustrated osmotic agent delivery device 40. Examples of suitable osmotic delivery devices are disclosed in U.S. Pat. Nos. 3,760,984; 3,845,770; 3,995,631 and 4,111,202, which disclosures are incorporated herein by reference.

In a second embodiment, the outer wall 41 is comprised of a diffusional membrane which is hydrated by the IV fluid 13. Only that portion of wall 41 which is submerged in the IV fluid 13 becomes hydrated. The beneficial agent 44 is able to diffuse through the hydrated portion of wall 41 into the IV fluid 13. When wall 41 is made of a diffusional membrane material, the beneficial agent 44 should be soluble in the IV fluid 13 and no drug delivery passageway 47 is provided in device 40. The composition of diffusional wall portion 41 may be selected from known diffusional membrane materials in accordance with the type of beneficial agent being delivered by device 40. In general, the diffusional wall 41 is comprised of a polymer that allows the drug or other beneficial agent 44 contained in device 40 to diffuse therethrough and into the IV fluid 13. When the IV fluid 13 contacts the exterior of the diffusional wall 41, the beneficial agent 44 diffuses through the portion of the membrane wall 41 that is wetted by the IV fluid 13. Representative diffusional polymers include olefin polymers, vinyl polymers, condensation polymers, addition polymers, rubber polymers and silicone polymers, and in particular, polyethylene, polypropylene, polyvinyl acetate, polyvinyl acetal, polyvinyl chloride, polyamides, polyesters, butadiene rubber, organo-silicone polymers and copolymers thereof.

When the device 40 delivers a hydrophilic drug, the diffusional wall 41 is preferably comprised of a hydrophilic or microporous material. Examples of suitable hydrophilic materials include polyurethanes, polyvinyl alcohols, polyamides and cellophane.

When device 40 delivers a lipophilic drug, the diffusional wall 41 is preferably comprised of a lipophilic material. Examples of suitable lipophilic materials include natural rubbers, silicone rubbers, Hytrel ® (a thermoplastic polyester elastomer sold by E. I. DuPont de Nemours of Wilmington, DE), ethylene vinyl acetate (EVA), polyvinyl chloride, and Kraton ® (a styrene-butadiene block copolymer sold by Shell Chemical Co. of Houston, TX).

When device 40 delivers a polypeptide, protein or other macro-molecule, the wall 41 is preferably comprised of a microporous material. The pores in the microporous material will generally have a size of less than about 0.2 microns, and preferably about 0.1 to 0.2 microns. Examples of suitable microporous materials include Celgard ® (a microporous polypropylene film sold by Celanese Chemical Co. of Dallas, TX) cellophane, glass frits, vycor glass, porous glass and microporous membranes of the type utilized in known elementary osmotic pumps.

As in the osmotically driven agent dispensing devices 40 utilizing semipermeable/microporous walls 41, the diffusional device also delivers beneficial agent 44 into fluid 13 at a rate that is variable and that is dependent upon the surface area of wall 41 that is exposed to (i.e., hydrated by) fluid 13 within chamber 34.

Thus when using either a semipermeable or a diffusional agent delivery device 40, a technician may accurately vary the delivery rate of agent 44 from device 40 by varying the air/liquid interface level 35 within chamber 34. When substantially the entire device 40 is submerged in IV fluid 13, the delivery device 40 will deliver beneficial agent 44 at a maximum rate. Conversely, when only a small portion of delivery device 40 is submerged in the IV fluid 13 (i.e., when the air/liquid interface level 35 is at a level lower than that shown in FIG. 2) the delivery device 40 will deliver beneficial agent 44 at a relatively low rate. As will be appreciated by those skilled in the art, the delivery rate of agent 44 can be easily adjusted simply by adjusting the air/liquid interface level 35 in relation to the markings 45 provided on device 40.

A third embodiment of an agent dispensing device (not shown in the figures) which may be used in the formulator 30 of the present invention comprises an agent-containing polymeric matrix. When the matrix is exposed to IV fluid 13, it releases the beneficial agent dispersed therein at a controlled rate. The rate of agent release is dependent upon the surface area of the matrix which is exposed to the IV fluid. Suitable polymeric matrices are known in the art and disclosed for example in U.S. Pat. Nos. 3,921,636; 4,066,747; 4,070,347; 4,190,642; 4,246,397; 4,281,654; 4,303,637; 4,304,765; 4,432,964; and 4,478,818. The disclosures of the relevant portions of these patents are incorporated herein by reference.

In the embodiment illustrated in FIG. 2, formulator 30 simultaneously acts as a drip chamber while housing the agent delivery device 40. The agent formulator 30 is used to achieve a desired drip flow rate of IV fluid 13. For example, the agent formulator 30 can have a fast drip rate for adults, or it can have a slower drip rate for pediatric use. The agent formulator 30 can be made with various sized inlets for controlling the rate of drip, or the drip rate can be controlled by a regulating clamp on the tubing conveying fluid thereto. The agent formulator 30 can deliver, for example from 2 to 75 drops per minute over a period of from 1 minute to 1 hour. More preferably, the therapist can adjust the rate of flow to between about 2 and 20 drops per minute, or for the needs of the patient.

Agent administration that is independent of intravenous fluid flow rate is extremely advantageous since careful control of the volumetric flow rate of intravenous fluid through the formulation chamber is not required. Hence, repeated adjustment of the flow by medical personnel, or the use of expensive, automated flow monitors is not needed. The operation also provides the advantage that the formulation of agent and intravenous fluid is carried out automatically in situ within formulator 30. The present invention eliminates the need to have the agent formulated into a parenteral solution by a pharmacist, and it also eliminates the need for the agent to be packaged separately from the intravenous fluid container 12. Another advantage provided by this invention is the ease with which the intravenous delivery system 10 can be sterilized. Since agent formulator 30 and the agent delivery device 40 are compatible with conventional sterilization techniques used to sterilize intravenous therapy systems, the agent formulator 30 and the agent delivery device 40 may be incorporated into the intravenous system 10 at the time of manufacture and sterilized therewith.

FIG. 3 illustrates another agent formulator designated 130. Formulator 130 comprises a wall 132 and a housing 150 holding a plurality of agent delivery devices 140a, 140b and 140c. The wall 132 and the housing 150 form an internal chamber 134. In this embodiment, the chamber 134 is continuously and completely filled with flowing IV fluid which enters through tubing 23 and exits out of tubing 25.

Each of the agent delivery devices 140 is movable within a cylindrical opening 151 in housing 150 in the direction of arrow A. Thus, each delivery device 140 may be extended into, or retracted from, chamber 134. One or more O-rings 152 provide a fluid-tight seal between the housing 150 and the delivery device 140. When wall 141 is composed of a semipermeable or microporous material, an agent delivery orifice 147 is provided in the end of device 140 which extends into the chamber 134. The position of the delivery devices 140 with respect to the O-rings 152 can be adjusted according to conventional means. The devices 140 and/or the housing 150 may be provided with markings 145 enabling a medical technician to accurately adjust the length of the device 140 that extends beyond the leftmost O-ring 152 into chamber 134 and thus, the area of wall 141 that is exposed to IV fluid in chamber 134.

In operation, IV fluid enters chamber 134 and is imbibed through the portion of semipermeable/microporous wall 141 which extends beyond the O-rings 152. The IV fluid is imbibed through the exposed portion of wall 141 into device 140 in a tendency towards osmotic equilibrium. IV fluid is imbibed by device 140 at a rate determined by the surface area of wall 141 which extends into chamber 134 beyond the O-rings 152, as well as by the permeability of the wall 141 and the osmotic gradient across the wall 141. The imbibed IV fluid forms a suspension or a solution of the beneficial agent that is dispensed through the delivery orifice 147 and into the IV fluid within chamber 134 over a prolonged period of time. The rate of agent delivery into the IV fluid is controlled mainly by the surface area of wall 141 which extends beyond the O-rings 152 into the chamber 134 and thus exposed to the IV fluid.

The lowermost delivery device 140c illustrates an alternate embodiment of the delivery device 140a. Delivery device 140c has an internal chamber which filled with a beneficial agent 144. The internal chamber is divided into three subchambers by dividers 148. The dividers 148 are impermeable to both the IV fluid and to the beneficial agent 144. Each of the three subchambers carries a predetermined dose of beneficial agent 144. When the wall 141 of delivery device 140c is composed of a semipermeable or microporous material which is substantially impermeable to the passage of agent 144, each subchamber of device 140c is provided with its own delivery orifice 147. Suitable markings may be provided on the exterior of delivery device 140c to enable a medical technician to expose only the leftmost subchamber (i.e., for delivery of a single predetermined dose of agent 144) to the IV fluid flowing through chamber 144. Once the first dose is completely delivered, the delivery device 140 can be extended further into chamber 134 to deliver second and third doses if desired.

A device 160, for adjustably positioning any of the three delivery devices 140, is also shown in conjunction with the delivery device 140c in FIG. 3. Device 160 comprises a micrometer-like device and includes a plunger 161 which is attached to one end of the delivery device 140c, a housing 162, a barrel 164 and a rotatable knob 166. By turning knob 166, the plunger 161 is extended into the opening 151, thereby pushing delivery device 140c into chamber 134. Markings 163 are provided on barrel 164 to enable a technician to determine the extent to which the delivery device 140c extends into chamber 134.

In a second embodiment, wall 141 is comprised of a diffusional membrane material. The delivery of beneficial agent into the IV fluid is achieved by the beneficial agent diffusing through the membrane wall 141 rather than IV fluid being imbibed therethrough. When delivery device 140 utilizes a diffusional wall 141, the beneficial agent must be soluble in the IV fluid and no delivery orifice 147 is provided. As with the semipermeable delivery device 140, the rate of delivery of beneficial agent from the diffusional delivery device 140 into the IV fluid is controlled by the surface area of wall 141 which extends beyond the O-rings 152 into the chamber 134 and thus exposed to the IV fluid.

In the configuration illustrated in FIG. 3 (and assuming that all three devices 140 are of identical construction and composition), the topmost delivery device 140 delivers beneficial agent at a relatively high rate (since a large percentage of its wall 141 is exposed to IV fluid), the middle delivery device 140 delivers beneficial agent at a medium rate, while the lowermost device 140 delivers beneficial agent at a negligible rate (since a negligible portion of its wall 141 is exposed to IV fluid). Of course, it is within the scope of the present invention to utilize one, two, three or more delivery devices 140 within a single formulator 130.

As an alternative to the semipermeable, microporous and diffusional delivery devices described heretofore, the delivery device 40 illustrated in FIG. 2 and the delivery devices 140 illustrated in FIG. 3 may be comprised of a polymer matrix containing a beneficial agent dispersed therein. The polymer matrix may be comprised of the same matrix materials described above in connection with device 40. The matrix can possess any shape such as rod, disk and the like that fits into chamber 134.

FIG. 4 illustrates another agent formulator designated 230. Formulator 230 comprises a wall 232 and a semipermeable or microporous membrane 241. A delivery orifice 247 is provided in the lowermost portion of membrane 241. Formulator 230 contains a beneficial agent 244 to be delivered into the IV fluid 13 which enters through tube 23 and exits through tube 25.

Membrane 241 may be comprised of the same or similar materials used to make the semipermeable/microporous outer wall 41 of device 40 illustrated in FIG. 2 and described above.

The beneficial agent 244 exhibits an osmotic pressure gradient across membrane 241 against the IV fluid 13 flowing through chamber 234. The beneficial agent 244 can comprise an agent that exhibits an osmotic pressure gradient or the agent 244 can comprise a drug mixed with an osmotically effective solute, such as sodium chloride, potassium chloride and the like, that exhibits an osmotic pressure substantially greater than the fluid in chamber 234.

Preferably, the wall 232 of formulator 230 is comprised of a transparent material, such as plastic or glass, enabling a medical technician to see the air/liquid interface level 235 within chamber 234. Suitable marking lines (not shown) may be provided along the length of wall 232 for setting the level 235 at the desired point.

Because membrane 241 is made of a semipermeable or microporous material that is permeable to the IV fluid 13, the rate at which IV fluid permeates through membrane 241 will be controlled by the surface area of membrane 241 that is exposed to the fluid 13 within chamber 234. Likewise, the rate at which the agent 244 is delivered from device 230 is controlled by the surface area of membrane 241 that is exposed to the fluid 13 within chamber 234. The air liquid interface level 235 can be adjusted using the same methods described above in connection with the adjustment of the air/liquid interface level 35 in formulator 30. An air release valve (not shown in FIG. 4) similar to valve 31 shown in FIG. 2 may optionally be provided in wall 232 to adjust the air/liquid interface level 235. Thus, by varying the air/liquid interface level 235 within chamber 234, a technician may accurately vary the delivery rate of agent 244 from device 230. As with device 40 shown in FIG. 2, the IV fluid 13 entering formulator 230 forms a suspension or a solution of agent 244 that is dispensed through orifice 247 over a prolonged period of time. The delivery rate of agent 244 into the IV fluid 13 is controlled by formulator 230 and is independent of the rate of IV fluid flow and the pH of the IV fluid in the chamber 234.

Alternatively, membrane 241 can be comprised of a diffusional membrane material similar to those described above in connection with the diffusional embodiments of delivery devices 40 and 140. When membrane 241 is comprised of a diffusional membrane material, no orifice 247 is provided. In addition, the beneficial agent 244 should be soluble in the IV fluid 13. As with the semipermeable/microporous delivery device, the rate of delivery of beneficial agent from the diffusional delivery device 230 into the IV fluid is controlled by the surface area of wall 241 which is exposed to the IV fluid.

As with the semipermeable, microporous and diffusional membrane-containing drug delivery devices 40 and 140 described earlier, device 230 can also take the form of a polymer matrix having a beneficial agent dispersed therein. The agent-containing polymer matrix is simply used in place of the membrane 241 and the agent 244 shown in FIG. 4. As in the semipermeable and diffusional devices 230, the rate at which the beneficial agent is delivered from the agent-containing polymer matrix device 230 is also dependent upon the surface area of the matrix which is exposed to the IV fluid. Thus, the rate at which a beneficial agent, such as a drug, is delivered into the flowing IV fluid can be controlled simply by adjusting the surface area of the matrix exposed to the fluid. This may be done by suitably adjusting the liquid level 235 of the IV fluid in chamber 234.

While there has been described features of the invention as applied to presently preferred embodiments, those skilled in the art will appreciate that various modifications, changes, additions, and omissions in the systems illustrated and described can be made without departing from the spirit of the invention, as defined in the appended claims.

I claim:

1. An agent formulator for use in a parenteral fluid delivery system, the formulator comprising:
    (a) a chamber having fluid inlet means connectable to a reservoir of a parenterally acceptable fluid, and fluid outlet means to maintain a continuous flow of the parenterally acceptable fluid therethrough;
    (b) an agent delivery device in the chamber, the delivery device containing an agent and having (i) a wall portion that is permeable to the parenteral fluid and substantially impermeable to the agent and (ii) a passageway through which the agent is delivered into the fluid, the wall portion having an area which is exposed to the fluid flowing through the chamber; and
    (c) means for adjustably varying the area of the wall portion which is exposed to the fluid flowing through the chamber;
    wherein in operation, the fluid flowing through the chamber contacts the wall portion, is imbibed through the wall portion and causes the agent to be delivered from the device through the passageway and into the flowing fluid, the agent being released at a rate which is variable, which is controlled substantially by the area of the wall portion exposed to the fluid and which is substantially independent of volumetric flow rate of the fluid flowing through the chamber.

2. The formulator of claim 1, wherein the agent is a drug and the parenteral fluid is an intravenously acceptable fluid.

3. The formulator of claim 1, wherein the delivery device comprises a semipermeable wall forming a compartment which contains the agent, the passageway comprising a delivery port extending through the wall.

4. The formulator of claim 1, wherein the chamber has a transparent wall, allowing the chamber to be simultaneously employed as a drip chamber for providing a measurable number of drops per minute of the fluid, the fluid transporting the agent released by the device to an agent receptor site.

5. The formulator of claim 1, wherein the chamber has a gas/liquid interface at a level within the chamber, the means for adjustably varying the area exposed to the flowing fluid comprising means for adjusting the level of the gas/liquid interface within the chamber and along the wall portion.

6. The formulator of claim 5, wherein the means for adjusting the gas/liquid interface level includes a valve for releasing gas from the chamber.

7. The formulator of claim 1, wherein the means for adjustably varying the area exposed to the flowing fluid comprises means for adjustably obstructing the area of the wall portion which is exposed to the flowing fluid.

8. The formulator of claim 7, wherein the adjustable obstructing means includes a fluid seal disposed along the wall portion and in sealing relationship thereto.

9. The formulator of claim 1, wherein the wall portion is comprised of a semipermeable membrane.

10. The formulator of claim 1, wherein the wall portion is comprised of a microporous membrane.

11. The formulator of claim 1, wherein the agent is osmotically active.

12. The formulator of claim 1, wherein the agent comprises a drug and an osmotically active solute.

13. A parenteral delivery system for administering an agent parenterally to an animal in which the agent is formulated in situ, comprising in combination:
    (1) a container of a pharmaceutically acceptable parenteral fluid that is a carrier for the agent;
    (2) a parenteral fluid administration set connected to the container for permitting the fluid to flow from the container through the administration set to the animal, the set comprising a drip chamber, tubing extending from the drip chamber to the animal, and an agent formulator connected into the tubing such that the intravenous fluid flows through the formulator;
    the formulator comprising:
    (a) a chamber having fluid inlet and outlet means to maintain a continuous flow of the parenteral fluid therethrough;
    (b) a delivery device in the chamber, the delivery device containing an agent and having (i) a wall portion that is permeable to the parenteral fluid and substantially impermeable to the agent and (ii) a delivery port through which the agent is delivered into the fluid, the wall portion having an area which is exposed to the fluid flowing through the chamber; and
    (c) means for adjustably varying the area of the wall portion which is exposed to the liquid flowing through the chamber;
    wherein in operation, the fluid flowing through the chamber contacts the wall portion, is imbibed through the wall portion and causes the agent to be delivered from the device through the delivery port and into the flowing fluid, the agent being released at a rate which is variable, which is controlled substantially by the area of the wall portion exposed to the fluid and which is substantially independent of volumetric flow rate of the liquid flowing through the chamber.

14. The parenteral delivery system of claim 13, wherein a skin piercing means is connected to the tubing for administering the agent formulation to the animal.

15. The parenteral delivery system of claim 13, wherein the animal is a human and the agent comprises a drug.

16. The parenteral delivery system of claim 13, wherein the parenteral fluid is an intravenously acceptable fluid.

17. A method for the controlled parenteral administration of a beneficial agent to an animal, which method comprises:
  (a) placing an agent delivery device in an agent formulation chamber, the chamber having an inlet communicating with a container of a pharmaceutically acceptable parenteral fluid and an outlet communicating with the animal, the delivery device containing the agent and having (i) a wall portion that is permeable to the parenteral fluid and substantially impermeable to the agent and (ii) a passageway through which the agent is delivered into the fluid;
  (b) allowing the parenteral fluid, which is a carrier for the agent, to flow from the container, through the chamber and into the animal;
  (c) adjustably varying the area of the wall portion which is exposed to the fluid flowing through the chamber;
wherein in operation, the fluid flowing through the chamber contacts the wall portion, is imbibed through the wall portion and causes the agent to be delivered from the device through the passageway and into the flowing fluid, the agent being released at a rate which is variable, which is controlled substantially by the area of the wall portion exposed to the fluid and which is substantially independent of volumetric flow rate of the fluid flowing through the chamber, thereby administering the agent to the animal in a beneficially effective amount over a prolonged period of time.

18. The method of claim 17, wherein a drip chamber is positioned between the container and the formulation chamber for measuring the number of drops of liquid conveyed from the container.

19. The method of claim 17, wherein the formulation chamber also comprises a drip chamber.

20. The method of claim 17, wherein the animal is a human and the agent is a drug.

21. An agent formulator for use in a parenteral fluid delivery system, the formulator comprising:
  (a) a chamber having fluid inlet means connectable to a reservoir of a parenterally acceptable fluid and fluid outlet means to maintain a continuous flow of the parenterally acceptable fluid therethrough;
  (b) an agent delivery device in the chamber, the delivery device containing an agent which is soluble in the fluid and a wall portion comprised of a diffusional material which is hydrated by the parenteral fluid and permits the agent to diffuse therethrough for delivery into the fluid, the wall portion having an area which is exposed to the fluid flowing through the chamber; and
  (c) means for adjustably varying the area of the wall portion which is exposed to the fluid flowing through the chamber;

wherein in operation, the fluid flowing through the chamber contacts the wall portion causing the agent to diffuse through the wall portion and into the flowing fluid, the agent being released at a rate which is variable, which is controlled substantially by the area of the wall portion exposed to the fluid and which is substantially independent of volumetric flow rate of the fluid flowing through the chamber.

22. The formulator of claim 21, wherein the agent is a drug and the parenteral fluid is an intravenously acceptable fluid.

23. The formulator of claim 21, wherein the chamber has a transparent wall, allowing the chamber to be simultaneously employed as a drip chamber for providing a measurable number of drops per minute of the fluid, the fluid transporting the agent released by the device to an agent receptor site.

24. The formulator of claim 21, wherein the chamber has a gas/liquid interface at a level within the chamber, the means for adjustably varying the area exposed to the flowing fluid comprising means for adjusting the level of the gas/liquid interface within the chamber and along the wall portion.

25. The formulator of claim 24, wherein the means for adjusting the gas/liquid interface level includes a valve for releasing gas from the chamber.

26. The formulator of claim 21, wherein the means for adjustably varying the surface area exposed to the flowing fluid comprises means for adjustably obstructing the surface area of the wall portion exposed to the flowing fluid.

27. The formulator of claim 26, wherein the adjustable obstructing means includes a fluid seal disposed along the wall portion and in sealing relationship thereto.

28. The formulator of claim 21, wherein the agent is osmotically active.

29. The formulator of claim 21, wherein the agent comprises a drug and an osmotically active solute.

30. A parenteral delivery system for administering an agent parenterally to an animal in which the agent is formulated in situ, comprising in combination:
  (1) a container of a pharmaceutically acceptable parenteral fluid that is a carrier for the agent;
  (2) a parenteral fluid administration set connected to the container for permitting the fluid to flow from the container through the administration set to the animal, the set comprising a drip chamber, tubing extending from the drip chamber to the animal, and an agent formulator connected into the tubing such that the intravenous fluid flows through the formulator;
the formulator comprising:
  (a) a chamber having fluid inlet and outlet means to maintain a continuous flow of the parenteral fluid therethrough;
  (b) a delivery device in the chamber, the delivery device containing an agent and having a wall portion comprised of a diffusional material which is hydrated by the parenteral fluid and permits the agent to diffuse therethrough for delivery into the fluid, the wall portion having an area which is exposed to the fluid flowing through the chamber; and
  (c) means for adjustably varying the area of the wall portion which is exposed to the fluid flowing through the chamber;

wherein in operation, the fluid flowing through the chamber contacts the wall portion causing the agent to diffuse through the wall portion and into the flowing fluid, the agent being released at a rate which is variable, which is controlled substantially by the area of the wall portion exposed to the fluid and which is substantially independent of volumetric flow rate of the fluid flowing through the chamber.

31. The parenteral delivery system of claim 30, wherein a skin piercing means is connected to the tubing for administering the agent formulation to the animal.

32. The parenteral delivery system of claim 30, wherein the animal is a human and the agent comprises a drug.

33. The parenteral delivery system of claim 30, wherein the parenteral fluid is an intravenously acceptable fluid.

34. A method for the controlled parenteral administration of a beneficial agent to an animal, which method comprises:
 (a) placing an agent delivery device in an agent formulation chamber, the chamber having an inlet communicating with a container of a pharmaceutically acceptable parenteral fluid and an outlet communicating with the animal, the delivery device containing the agent and having a wall portion comprised of a material which is hydrated by the parenteral fluid and permits the agent to diffuse therethrough for delivery into the fluid;
 (b) allowing the parenteral fluid, which is a carrier for the agent, to flow from the container, through the chamber and into the animal;
 (c) adjustably varying the area of the wall portion which is exposed to the fluid flowing through the chamber;
wherein in operation, the fluid flowing through the chamber contacts the wall portion causing the agent to diffuse through the wall portion and into the flowing fluid, the agent being released at a rate which is variable, which is controlled substantially by the area of the wall portion exposed to the fluid and which is substantially independent of volumetric flow rate of the fluid flowing through the chamber, thereby administering the agent to the animal in a beneficially effective amount over a prolonged period of time.

35. The method of claim 34, wherein a drip chamber is positioned between the container and the formulation chamber for measuring the number of drops of liquid conveyed from the container.

36. The method of claim 34, wherein the formulation chamber also comprises a drip chamber.

37. The method of claim 34, wherein the animal is a human and the agent is a drug.

38. An agent formulator for use in a parenteral fluid delivery system, the formulator comprising:
 (a) a chamber having fluid inlet means connectable to a reservoir of a parenterally acceptable fluid, and fluid outlet means to maintain a continuous flow of the parenterally acceptable fluid therethrough;
 (b) an agent delivery device in the chamber, the delivery device comprising a polymer matrix containing an agent, the matrix having an area which is exposed to the fluid flowing through the chamber, the agent being delivered into the fluid upon exposure of the matrix to the parenteral fluid; and
 (c) means for adjustably varying the area of the matrix which is exposed to the fluid flowing through the chamber;
wherein in operation, the fluid flowing through the chamber contacts the agent-containing matrix, causing the agent to be released by the matrix into the flowing fluid, the agent being released at a rate which is variable, which is controlled substantially by the area of the matrix exposed to the fluid and which is substantially independent of volumetric flow rate of the fluid flowing through the chamber.

39. The formulator of claim 38, wherein the agent is a drug and the parenteral fluid is an intravenously acceptable fluid.

40. The formulator of claim 38, wherein the chamber has a transparent wall, allowing the chamber to be simultaneously employed as a drip chamber for providing a measurable number of drops per minute of the fluid, the fluid transporting the agent released by the device to an agent receptor site.

41. The formulator of claim 38, wherein the chamber has a gas/liquid interface at a level within the chamber, the means for adjustably varying the area exposed to the flowing fluid comprising means for adjusting the level of the gas/liquid interface within the chamber and along the matrix.

42. The formulator of claim 41, wherein the means for adjusting the gas/liquid interface level includes a valve for releasing gas from the chamber.

43. The formulator of claim 38, wherein the means for adjustably varying the area exposed to the flowing fluid comprises means for adjustably obstructing the area of the matrix exposed to the flowing fluid.

44. The formulator of claim 43, wherein the adjustable obstructing means includes a fluid seal disposed along the matrix in sealing relationship thereto.

45. The formulator of claim 38, wherein the agent is osmotically active.

46. The formulator of claim 38, wherein the agent comprises a drug and an osmotically active solute.

47. A parenteral delivery system for administering an agent parenterally to an animal in which the agent is formulated in situ, comprising in combination:
 (1) a container of a pharmaceutically acceptable parenteral fluid that is a carrier for the agent;
 (2) a parenteral fluid administration set connected to the container for permitting the fluid to flow from the container through the administration set to the animal, the set comprising a drip chamber, tubing extending from the drip chamber to the animal, and an agent formulator connected into the tubing such that the intravenous fluid flows through the formulator;
the formulator comprising:
 (a) a chamber having fluid inlet means connected to the container of pharmaceutically acceptable parenteral fluid, and fluid outlet means to maintain a continuous flow of the parenteral fluid therethrough;
 (b) an agent delivery device in the chamber, the delivery device comprising a polymer matrix containing an agent, the matrix having an area which is exposed to the fluid flowing through the chamber, the agent being delivered into the fluid upon exposure of the matrix to the parenteral fluid; and
 (c) means for adjustably varying the area of the matrix which is exposed to the liquid flowing through the chamber;

wherein in operation, the fluid flowing through the chamber contacts the agent-containing matrix, causing the agent to be released by the matrix into the flowing fluid, the agent being released at a rate which is variable, which is controlled substantially by the area of the matrix exposed to the fluid and which is substantially independent of volumetric flow rate of the liquid flowing through the chamber.

48. The parenteral delivery system of claim 47, wherein a skin piercing means is connected to the tubing for administering the agent formulation to the animal.

49. The parenteral delivery system of claim 47, wherein the animal is a human and the agent comprises a drug.

50. The parenteral delivery system of claim 47, wherein the parenteral fluid is an intravenously acceptable fluid.

51. A method for the controlled parenteral administration of a beneficial agent to an animal, which method comprises:

(a) placing an agent delivery device in an agent formulation chamber, the chamber having an inlet communicating with a container of a pharmaceutically acceptable parenteral fluid and an outlet communicating with the animal, the delivery device comprising a polymer matrix containing the agent dispersed therein, the agent being delivered into the fluid upon exposure of the matrix to the parenteral fluid;

(b) allowing the parenteral fluid, which is a carrier for the agent, to flow from the container, through the chamber and into the animal;

(c) adjustably varying the area of the matrix which is exposed to the fluid flowing through the chamber;

wherein in operation, the fluid flowing through the chamber contacts the matrix, causing the agent to be released by the matrix into the flowing fluid, the agent being released at a rate which is variable, which is controlled substantially by the area of the matrix exposed to the fluid and which is substantially independent of volumetric flow rate of the fluid flowing through the chamber, thereby administering the agent to the animal in a beneficially effective amount over a prolonged period of time.

52. The method of claim 51, wherein a drip chamber is positioned between the container and the formulation chamber for measuring the number of drops of liquid conveyed from the container.

53. The method of claim 51, wherein the formulation chamber also comprises a drip chamber.

54. The method of claim 51, wherein the animal is a human and the agent is a drug.

* * * * *